United States Patent
Macken et al.

(10) Patent No.: US 10,105,539 B2
(45) Date of Patent: Oct. 23, 2018

(54) CONFIGURING A STIMULATION UNIT OF A HEARING DEVICE

(71) Applicant: Cochlear Limited, Macquarie University, NSW (AU)

(72) Inventors: Luk Macken, Antwerp (BE); Frédéric Goddeeris, Meerbeke (BE); Koen Van Herck, Kontich (BE)

(73) Assignee: Cochlear Limited, Macquarie University, NSW (AU)

( * ) Notice: Subject to any disclaimer, the term of this patent is extended or adjusted under 35 U.S.C. 154(b) by 186 days.

(21) Appl. No.: 14/972,627

(22) Filed: Dec. 17, 2015

(65) Prior Publication Data

US 2016/0175593 A1 Jun. 23, 2016

Related U.S. Application Data (60) Provisional application No. 62/093,123, filed on Dec. 17, 2014.

(51) Int. Cl.
*A61N 1/00* (2006.01)
*A61N 1/36* (2006.01)
(Continued)

(52) U.S. Cl.
CPC ..... *A61N 1/36032* (2013.01); *A61N 1/36036* (2017.08); *H04R 25/70* (2013.01);
(Continued)

(58) Field of Classification Search
CPC .............. A61N 1/0541; A61N 1/36032; A61N 1/36036; A61N 1/36128; H04R 2225/55;
(Continued)

(56) References Cited

U.S. PATENT DOCUMENTS

| 4,532,930 A | 8/1985 | Crosby et al. |
| 4,776,322 A | 10/1988 | Hough et al. |

(Continued)

FOREIGN PATENT DOCUMENTS

| DE | 19915846 C1 | 8/2000 |
| EP | 0730882 A2 | 9/1996 |

(Continued)

*Primary Examiner* — George Manuel
(74) *Attorney, Agent, or Firm* — Pilloff & Passino LLP; Martin J. Cosenza (57) ABSTRACT

Disclosed herein are methods, systems, and devices for configuring a stimulation unit of a hearing device by determining whether the stimulation unit can process received stimulation data. In an example method, the stimulation unit receives one or more data signals, which comprise at least one stimulation signal that includes stimulation data, and processes one of the data signals to determine whether it can process the stimulation data in order to generate one or more stimuli. If the stimulation unit can process the stimulation data, the method includes operating the stimulation unit in a normal mode, in which case the stimulation unit processes the stimulation data to generate the one or more stimuli. On the other hand, if the stimulation unit cannot process the stimulation data, the method includes operating the stimulation in a safe mode, in which case the stimulation unit does not process the stimulation data.

24 Claims, 6 Drawing Sheets

(51) Int. Cl.
*H04R 25/00* (2006.01)
*A61N 1/05* (2006.01)

(52) U.S. Cl.
CPC ........ *A61N 1/0541* (2013.01); *A61N 1/36128* (2013.01); *H04R 25/606* (2013.01); *H04R 2225/55* (2013.01); *H04R 2225/67* (2013.01); *H04R 2460/13* (2013.01)

(58) Field of Classification Search
CPC ............ H04R 2225/67; H04R 2460/13; H04R 25/606; H04R 25/70
See application file for complete search history.

(56) References Cited

U.S. PATENT DOCUMENTS

| | | |
|---|---|---|
| 5,266,919 A | 11/1993 | Cook et al. |
| RE34,961 E | 6/1995 | Widin et al. |
| 5,569,307 A | 10/1996 | Schulman et al. |
| 5,571,148 A | 11/1996 | Loeb et al. |
| 5,619,580 A | 4/1997 | Hansen |
| 5,690,690 A | 11/1997 | Nappholz et al. |
| 5,800,473 A | 9/1998 | Faisandier |
| 5,817,137 A | 10/1998 | Kaemmerer |
| 5,891,180 A | 4/1999 | Greeninger et al. |
| 5,941,905 A | 8/1999 | Single |
| 6,072,884 A | 6/2000 | Kates |
| 6,118,877 A | 9/2000 | Lindemann et al. |
| 6,134,329 A | 10/2000 | Gao et al. |
| 6,195,585 B1 | 2/2001 | Karunasiri et al. |
| 6,198,971 B1 | 3/2001 | Leysieffer |
| 6,219,427 B1 | 4/2001 | Kates et al. |
| 6,219,580 B1 | 4/2001 | Faltys et al. |
| 6,243,608 B1 | 6/2001 | Pauly et al. |
| 6,308,099 B1 | 10/2001 | Fox et al. |
| 6,285,909 B1 | 11/2001 | Sweeney et al. |
| 6,327,501 B1 | 12/2001 | Levine et al. |
| 6,390,971 B1 | 5/2002 | Adams et al. |
| 6,434,247 B1 | 8/2002 | Kates et al. |
| 6,443,891 B1 | 9/2002 | Grevious |
| 6,482,154 B1 | 11/2002 | Haubrich et al. |
| 6,537,200 B2 | 3/2003 | Leysieffer et al. |
| 6,553,263 B1 | 4/2003 | Meadows et al. |
| 6,565,503 B2 | 5/2003 | Leysieffer et al. |
| 6,575,894 B2 | 6/2003 | Leysieffer et al. |
| 6,687,377 B2 | 2/2004 | Voix et al. |
| 6,697,674 B2 | 2/2004 | Leysieffer |
| 6,740,075 B2 | 5/2004 | Lebel et al. |
| 6,792,114 B1 | 9/2004 | Kates et al. |
| 6,738,670 B1 | 10/2004 | Almendinger et al. |
| 7,010,135 B2 | 3/2006 | Von Buol |
| 7,058,182 B2 | 6/2006 | Kates et al. |
| 7,120,500 B1 * | 10/2006 | Seligman ............... A61N 1/378 607/29 |
| 7,346,397 B2 | 3/2008 | Money et al. |
| 7,463,745 B2 | 12/2008 | Miller, III |
| 7,502,653 B2 | 3/2009 | Daly |
| 7,536,022 B2 | 5/2009 | Von Buol |
| 7,664,281 B2 | 2/2010 | Merks et al. |
| 7,688,983 B2 | 3/2010 | Voix et al. |
| 8,229,127 B2 | 7/2012 | Jørgensen et al. |
| 8,243,939 B2 | 8/2012 | Perman |
| 8,254,586 B2 | 8/2012 | Voix et al. |
| 8,254,587 B2 | 8/2012 | Voix et al. |
| 8,315,708 B2 | 11/2012 | Berthelsdorf et al. |
| 2001/0033664 A1 | 10/2001 | Poux et al. |
| 2004/0024429 A1 | 2/2004 | Daly |
| 2004/0176822 A1 | 9/2004 | Thompson et al. |
| 2005/0163331 A1 | 7/2005 | Gao et al. |
| 2006/0020304 A1 | 1/2006 | Torgerson et al. |
| 2008/0260171 A1 | 10/2008 | Nordahn et al. |
| 2009/0067654 A1 | 3/2009 | Klinkby et al. |
| 2009/0147977 A1 | 6/2009 | Lamm et al. |
| 2009/0306742 A1 | 12/2009 | Van Dijk et al. |
| 2009/0316922 A1 | 12/2009 | Merks et al. |
| 2010/0016922 A1 | 1/2010 | Daly |
| 2010/0114288 A1* | 5/2010 | Haller ................ A61B 17/3468 607/137 |
| 2010/0172507 A1 | 7/2010 | Merks |
| 2010/0177917 A1 | 7/2010 | Van Der Werf |
| 2010/0232634 A1 | 9/2010 | Boldt |
| 2010/0296680 A1 | 11/2010 | Korl et al. |
| 2010/0310103 A1 | 12/2010 | Baechler et al. |
| 2011/0026746 A1 | 2/2011 | Baechler et al. |
| 2011/0166632 A1* | 7/2011 | Delp ................... A61N 5/0601 607/88 |
| 2012/0059435 A1 | 3/2012 | Daly |
| 2012/0189130 A1 | 7/2012 | Lee et al. |
| 2013/0006042 A1 | 1/2013 | Hillbratt et al. |
| 2013/0023960 A1* | 1/2013 | Stafford ............... A61N 5/0622 607/88 |
| 2014/0177890 A1 | 6/2014 | Höjlund et al. |
| 2014/0363036 A1 | 12/2014 | Hillbratt et al. |

FOREIGN PATENT DOCUMENTS

| | | |
|---|---|---|
| EP | 1830603 A2 | 9/2007 |
| EP | 2136575 A2 | 12/2009 |
| EP | 2189006 B1 | 6/2011 |
| WO | 0072917 A1 | 12/2000 |
| WO | 0103622 A1 | 1/2001 |
| WO | 0106810 A1 | 1/2001 |
| WO | 0113991 A1 | 3/2001 |
| WO | 2003003956 A1 | 1/2003 |
| WO | 2003009207 A1 | 1/2003 |
| WO | 2008/000843 A2 | 1/2008 |

* cited by examiner

CONFIGURING A STIMULATION UNIT OF A HEARING DEVICE

CROSS-REFERENCE TO RELATED APPLICATIONS

This application claims priority to Provisional U.S. Patent Application No. 62/093,123, entitled Configuring a Stimulation Unit of a Hearing Device, filed on Dec. 17, 2014, naming Luk Macken of Belgium as an inventor, the entire contents of that application being incorporated herein by reference in its entirety.

BACKGROUND

Unless otherwise indicated herein, the information described in this section is not prior art to the claims and is not admitted to be prior art by inclusion in this section.

Various types of hearing devices provide people with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

People with some forms of conductive hearing loss may benefit from hearing devices such as hearing aids or electromechanical hearing devices. A hearing aid, for instance, typically includes at least one small microphone to receive sound, an amplifier to amplify certain portions of the detected sound, and a small speaker to transmit the amplified sounds into the person's ear. An electromechanical hearing device, on the other hand, typically includes at least one small microphone to receive sound and a mechanism that delivers a mechanical force to a bone (e.g., the recipient's skull, or a middle-ear bone such as the stapes) or to a prosthetic (e.g., a prosthetic stapes implanted in the recipient's middle ear), thereby causing vibrations in cochlear fluid.

Further, people with certain forms of sensorineural hearing loss may benefit from hearing devices such as cochlear implants and/or auditory brainstem implants. Cochlear implants, for example, include at least one microphone to receive sound, a unit to convert the sound to a series of electrical stimulation signals, and an array of electrodes to deliver the stimulation signals to the implant recipient's cochlea so as to help the recipient perceive sound. Auditory brainstem implants use technology similar to cochlear implants, but instead of applying electrical stimulation to a person's cochlea, they apply electrical stimulation directly to a person's brain stem, bypassing the cochlea altogether, still helping the recipient perceive sound.

In addition, some people may benefit from hearing devices that combine one or more characteristics of the acoustic hearing aids, vibration-based hearing devices, cochlear implants, and auditory brainstem implants to perceive sound.

Hearing devices such as these typically include an external processing unit that typically performs at least some sound-processing functions and an internal stimulation unit that at least delivers a stimulus to a body part in an auditory pathway of the recipient. The auditory pathway includes a cochlea, an auditory nerve, a region of the recipient's brain, or any other body part that contributes to the perception of sound. In the case of a totally implantable hearing device, the stimulation unit includes both processing and stimulation components, though the external unit may still perform some processing functions when communicatively coupled or connected to the stimulation unit.

SUMMARY

Before a recipient uses a hearing device, an audiologist or other clinical specialist may calibrate, or "fit," the hearing device to the recipient. Generally speaking, each recipient of a hearing device has in one ear a specific amount of hearing loss. Moreover, for a recipient with hearing loss in both ears, the hearing loss in the recipient's right ear often differs from the hearing loss in the recipient's left ear. Thus, fitting a hearing prosthesis to a recipient may involve determining one or more stimulation profiles, which are sometimes referred to as "maps," that each include a set of a parameters used to generate stimuli that cause the recipient to perceive sound at one or more frequencies. The stimulation profiles may thus be based on a recipient's hearing loss in one ear, and each stimulation profile may be configured for a particular acoustic environment or situation.

The present disclosure addresses scenarios in which the stimulation unit can perform some signal processing. In such scenarios, an audiologist (or other clinical specialist) may load at least a portion of each determined stimulation profile into an external processing unit and at least a portion of each stimulation profile may be loaded into an implanted stimulation unit. For example, the portion of each stimulation profile loaded into the external unit may allow the external unit to determine amplitudes of one or more stimuli that will cause the recipient to perceive a portion of a received sound, whereas the portion of each stimulation profile loaded into the stimulation unit may allow the stimulation unit to convert the determined amplitudes to specific electrical, electromechanical, and/or electroacoustic stimuli in order to generate the one or more stimuli. During operation, the external unit may thus select a stimulation profile and process sounds using the selected user profile to generate stimulation data, which the external unit transmits to the stimulation unit. The external unit may also transmit with the stimulation data a stimulation profile identifier for the selected stimulation profile. The stimulation unit, in turn, may then use the selected stimulation profile to process the stimulation data, thereby generating stimuli that enable the recipient to perceive sound.

In some situations, however, the stimulation unit may not have access to the selected stimulation profile. If an update is applied to the external unit but not the stimulation unit, for instance, the external unit could select a stimulation profile that is not loaded into the stimulation unit. Alternatively, the stimulation unit could receive stimulation data generated by an external unit that is not associated with the stimulation unit. In this case, the received stimulation profile identifier could correspond to one of the stimulation profiles loaded into the stimulation unit, but the stimulation data will not be tailored to the recipient's ear. For instance, consider a situation in which a recipient has bilateral hearing devices, i.e., a first hearing device for the recipient's right ear and a second hearing device for the recipient's left ear. The recipient could accidentally couple the external unit of one hearing device to the stimulation unit of the other hearing device. Or a recipient could accidentally couple another recipient's external unit to the stimulation unit. In either of these situations, the stimulation unit would receive stimulation data generated using a user profile that is not calibrated for the ear in which the stimulation unit is implanted. Should the stimulation unit process such stimulation data, the resulting stimuli could impede the recipient's ability to perceive sounds or possibly cause the recipient discomfort.

In accordance with the present disclosure, the stimulation unit may periodically verify that it can properly process received stimulation data. By way of example, the stimulation unit may be associated with a specific external unit. The stimulation unit may then periodically verify that the associated external unit generated the received stimulation data and that the stimulation unit has access to the selected stimulation profile. If the stimulation verifies that both the associated external unit generated the received stimulation data and the stimulation unit has access to the selected stimulation profile, then the stimulation unit may operate in a normal mode. In the normal mode, the stimulation unit processes the received stimulation data unit using the selected stimulation profile to generate and deliver to the recipient one or more stimuli.

On the other hand, if the associated external unit did not generate the received stimulation data, or if the stimulation unit does not have access to the selected stimulation profile, the stimulation unit does not operate in the normal operating mode. Instead, the stimulation unit operates in a safe mode. In general, the stimulation unit provides a more limited set of functionalities in the safe mode than in the normal mode. By way of example, the stimulation unit may process the stimulation data using a default stimulation profile. Although the default stimulation profile may not provide optimal stimuli for the acoustic environment, using the default stimulation profile allows the stimulation unit to continue providing the recipient with stimuli. Alternatively, the stimulation unit may not generate stimuli based on received stimulation data in the safe mode. In either example, the stimulation unit can also provide the recipient with an indication of the stimulation unit not processing the received stimulation data, perhaps by causing the recipient to perceive an audible alarm or by causing the external unit to output a visual alarm. And in an example in which the stimulation unit is a totally implantable hearing device (e.g., the stimulation unit can detect and process an ambient sound without the external unit), the stimulation unit can generate stimuli based on sounds received at the implanted audio transducer when the stimulation unit cannot process the received stimulation data.

Accordingly, in one respect, disclosed herein is a method operable by a stimulation unit of a hearing device to facilitate such functionality. The method includes receiving at a stimulation unit of a hearing device receives one or more data signals. The one or more data signals comprise at least one stimulation signal that includes stimulation data. The method also includes the stimulation unit processing a data signal included in the one or more data signals to determine whether the stimulation unit is a target stimulation unit for the one or more data signals. Additionally, the method includes the stimulation unit operating in one of (i) a normal mode if the stimulation unit is the target stimulation unit of the one or more data signals or (ii) a safe mode if the stimulation unit is not the target stimulation unit of the one or more data signals. Operating in the normal mode comprises the stimulation unit using an active stimulation profile to process the stimulation data; based on the processed stimulation data, generating the one or more stimuli; and delivering the one or more stimuli to the recipient. By contrast, operating in the safe mode comprises the stimulation unit not processing the stimulation data using the active stimulation profile.

In another respect, disclosed herein is a non-transitory computer-readable medium having stored therein instructions executable by a computing device to cause the computing device to perform functions. The functions include determining whether a first identifier matches a second identifier, with the first identifier being included in a data signal transmitted by an external unit of a hearing device and the second identifiers being accessible to a stimulation unit of the hearing device. If at least the first identifier matches the second identifier, the functions then include (i) processing stimulation data generated by the processing unit to provide one or more stimuli configured to cause a recipient to perceive at least portion of a sound, and (ii) causing a stimulation component of the stimulation unit to deliver the one or more stimuli to the recipient. But if the first identifier does not match the second identifier, then the functions comprise not processing the stimulation data.

In yet another respect, disclosed herein is a stimulation unit of a hearing device. The stimulation unit comprises a data storage configured to store at least two available stimulation profiles, with each available stimulation profile including a set of fixed parameters for generating a plurality of stimuli. The stimulation unit also includes a stimulation component configured to stimulate a body part in an auditory pathway of the recipient. Further, the stimulation unit includes a processor configured to receive and process a stimulation signal, with the stimulation signal including stimulation data and information indicative of an active stimulation profile. The processor is also configured to access the data storage to determine that the active stimulation profile is one of the at least two internal stimulation profiles, to determine, based on the stimulation data and using the active stimulation profile, a stimulus deliverable by the stimulation component to the recipient, and to cause the stimulation component to deliver the determined stimulus to the recipient.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

DETAILED DESCRIPTION

Figure 1:
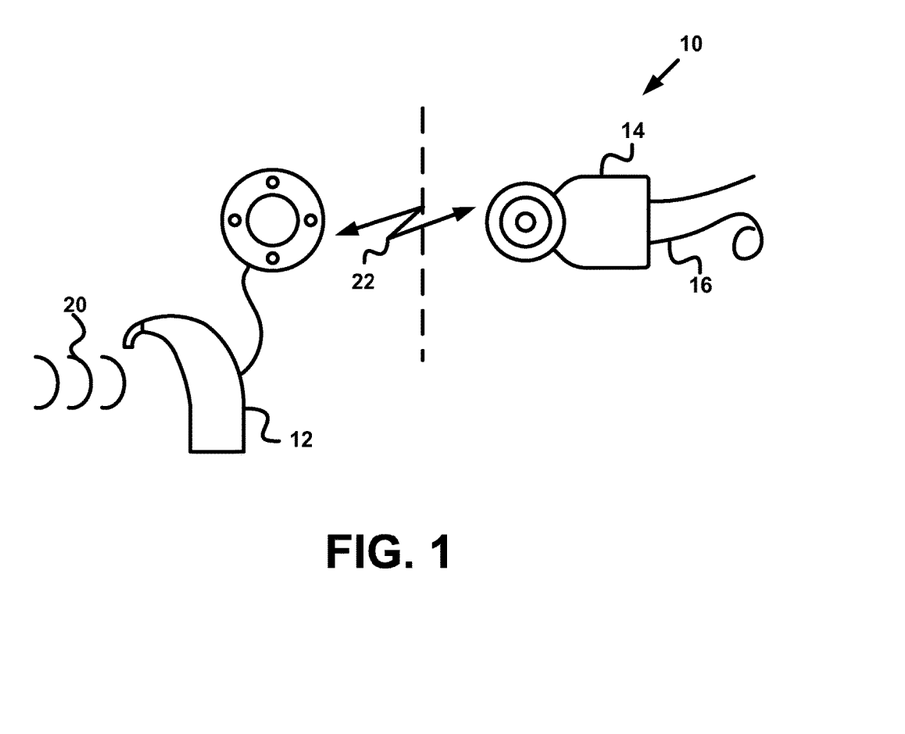
FIG. 1 is a simplified block diagram of an example system in which features of the present disclosure can be implemented.

Referring to the drawings, as noted above, FIG. 1 is a simplified illustration of a system in which features of the present disclosure can be implemented. In particular, FIG. 1 depicts a hearing device 10 that includes an external unit 12 and a stimulation unit 14. By way of example, the hearing device 10 is depicted as a cochlear implant. In this case, the stimulation unit 14 includes an electrode array 16 configured to stimulate one of the recipient's cochleae. Specifically, the electrode array 16 may include a plurality of electrodes, each of which corresponds to a frequency channel. The stimulation unit 14 may cause one or more of the electrodes to deliver an electrical stimulus to a region of the cochlea, thereby causing the recipient to perceive sound at a particular frequency. In other examples, however, the hearing device 10 may be a different type of hearing device. For instance, if the hearing device 10 is an auditory brainstem implant, the electrode array 16 may be adapted to be inserted into a portion of the recipient's brain. Or in examples in which the hearing device 10 does not deliver electrical stimuli to the recipient, a different stimulation component such as a transducer of a bone conduction device would replace the electrode array 16. Further, the stimulation unit 14 may not necessarily be implanted in the recipient's body in each embodiment of the hearing device 10. For example, the stimulation unit 14 might be inserted in one of the recipient's ear canals when the recipient uses the hearing device 10.

The external unit 12 receives and processes sounds, such as sound 20, to generate stimulation data, and the external unit 12 then transmits to the stimulation unit 14 the stimulation data, and potentially other data, via a link 22. The link 22 is preferably a wireless link that facilitates communicating with and transferring power to the stimulation unit 14, such as an inductive link or perhaps a 2.4 GHz radio frequency link. Other examples of the link 22 are possible as well.

To facilitate generating and processing the stimulation data, at least a portion of one or more stimulation profiles—each of which is specific to the same ear of the recipient—may be loaded into the external unit 12 and the stimulation unit 14 before the recipient uses the hearing device 10. By way of example, the one or more stimulation profiles could include a stimulation profile for a noisy acoustic environment, a stimulation profile for a quiet acoustic environment, a stimulation profile for conversational speech (e.g., a situation in which the recipient is conversing with another person), a stimulation profile for processing audio while the recipient is watching television, and/or a stimulation profile for processing audio received directly from a remote device (e.g., a smartphone, a telephone, a media-streaming device). Note that the listed examples of stimulation profiles are illustrative in nature and do not represent an exclusive list of possible stimulation profiles.

Each of the external unit 12 and the stimulation unit 14 may thus have access to a plurality of available stimulation profiles. Preferably, each stimulation profile is associated with a stimulation profile identifier that is used to identify that stimulation profile in the plurality of available stimulation profiles. In some examples, however, each stimulation profile may be identified by another means, such as by a storage location in a data storage of the external unit 12 and/or the stimulation unit 14.

To generate the stimulation data, the external unit 12 may process the sound 20 to select an active stimulation profile that the external unit 12 will use to generate stimulation data and that the stimulation unit 14 will use to generate one or more stimuli. To select the active stimulation profile, the external unit 12 may, for instance, analyze spectral information of the sound 20 (i.e., the energy of the sound 20 over a range of frequencies) over a series of samples or time intervals. Based on the analysis, the external unit 12 may select from the plurality of available stimulation profiles a stimulation profile best suited for processing sounds in the particular acoustic environment. The external unit 12 may then use the active stimulation profile to generate stimulation data based on the received sound, and the external unit 12 may then send to the stimulation unit 14 the stimulation data via the link 22. By way of example, the stimulation data may provide an indication of an amplitude level for a stimulus corresponding to each of one or more electrodes or frequency channels. Further, the external unit 12 may periodically send to the stimulation unit 14 data indicative of the active stimulation profile, perhaps by transmitting such data with stimulation data.

The stimulation unit 14 may thus receive the stimulation data and determine whether it is the target stimulation unit of the stimulation data. When the stimulation unit 14 determines that it can process the received stimulation data, the stimulation unit 14 operates in the normal mode, in which case the stimulation unit 14 by processing the received stimulation data using the active stimulation profile to generate one or more stimuli. If the stimulation data includes an amplitude level for an electrode (or frequency channel), for example, the stimulation unit 14 may access the active stimulation profile to determine an amplitude of electrical stimulus corresponding to the amplitude level for that electrode (or frequency channel). The stimulation unit 14 may then generate an electrical signal having the determined amplitude, which is subsequently delivered to the recipient via the electrode array 16.

In practice, the stimulation unit 14 normally operates in the normal mode but could operate in the safe mode in any of several scenarios. For instance, the stimulation unit 14 may receive stimulation data from an external unit other than the external unit 12, such as a stimulation device that belongs to another recipient or is calibrated for the recipient's other ear (if the recipient uses bilateral hearing devices). In either case, the stimulation unit 14 will not have access to the active stimulation profile used by the external unit to generate stimulation data. As a result, the stimulation unit 14 may determine that the stimulation unit 14 did not receive the data (stimulation or otherwise) from the associated external unit and, as a result, operate in the safe mode.

In another scenario, the recipient or an audiologist may load a new stimulation profile into the external unit 12 but not into the stimulation unit 14. If the external unit 12 selects the new stimulation profile as the active stimulation profile, the stimulation unit 14 may determine, upon receiving data from the external unit 12, that the plurality of available stimulation profiles does not include the new stimulation profile. The stimulation unit 14 could make such a determination by determining that a stimulation profile identifier for the active stimulation profile does not correspond to a stimulation profile identifier for a stimulation profile included in the plurality of available stimulation profiles. As in the previous scenario, the stimulation unit 14 operates in the safe mode when the stimulation unit 14 does not have access to the active stimulation profile. Other scenarios in which the stimulation unit 14 determines that it should not process the stimulation data are possible as well.

While operating in the safe mode, the stimulation unit 14 does not generate stimuli based on the received stimulation data. Instead, the stimulation unit 14 may generate one or more stimuli configured to cause the recipient to perceive an audible alarm indicative of the stimulation unit 14 operating in the safe mode, thereby alerting the recipient that the stimulation unit 14 is not operating normally. The audible alarm could cause the recipient to perceive one or more tones or sequences of tones, or the audible alarm could cause the recipient to perceive a spoken word or phrase. Further, the audible alarm could provide the recipient with an indication of the condition that caused the stimulation unit 14 to operate in the safe mode (e.g., whether the wrong external unit is coupled to the stimulation unit 14 or whether the correct external unit is using an unavailable stimulation profile as the active stimulation profile).

Alternatively, the stimulation unit 14 may process the received stimulation data using a default stimulation profile. The default stimulation profile may include a set of parameters that allow the stimulation unit 14 to generate, based on the received stimulation data, one or more stimuli within a set of stimulus levels that will not cause the recipient discomfort. While the default stimulation profile may not provide an optimal set of stimuli for a given acoustic environment, using the default stimulation profile allows the stimulation unit 14 to generate stimuli based on the received stimulation data event though the stimulation unit is not associated with the external unit that generated the received stimulation data. In the same manner, the stimulation unit 14 can use the default stimulation profile when the stimulation unit does not have access to the active stimulation profile.

Further, the stimulation unit 14 could be a totally implantable hearing device, in which case the stimulation unit 14 includes audio detection and processing capabilities. A totally implantable hearing prosthesis has the ability to receive and process sounds to generate one or more stimuli without an external microphone or sound processor. In these examples, the stimulation unit 14 includes a sound processor and one or more implanted microphones (or other audio transducers). Although in some situations the quality of the perceived sound may not be as good as when the stimuli are based on stimulation data received from an external sound processor, generating the one or more stimuli based on sounds detected by the implanted audio transducers may still allow the recipient to perceive at least some ambient sound. The recipient may also perceive a difference in sound quality when the stimulation unit switches from stimuli based on externally-received sounds to stimuli based on internally received sounds, which could also alert the recipient to the fact that the stimulation unit 14 is operating in the safe mode.

The stimulation unit 14 may still receive and process data while in the operating mode, and may subsequently return to the normal mode upon determining either that the stimulation unit 14 is the target stimulation unit or that the active stimulation profile is included in the plurality of available stimulation profiles. If the recipient had accidentally coupled the external unit to the stimulation unit 14, for instance, the stimulation unit 14 may operate in the normal mode after the recipient replaces the external unit with the external unit 12. Alternatively, the stimulation unit 14 might wait for an initialization signal from the external unit 12 before returning to the normal mode. As another example, the stimulation unit 14 could return to the normal mode upon determining that the selected active stimulation profile is included in the plurality of available stimulation profiles.

In this manner, the stimulation unit 14 may provide safe processing of stimulation data. Additionally, verifying that the stimulation unit 14 can process received stimulation data may advantageously allow the external unit 12 to transmit stimulation signals without the stimulation unit 14 acknowledging receipt of each stimulation signal, thereby avoiding situations in which the external unit retransmits stimulation data that the stimulation unit had properly received (which might otherwise happen if interference prevents the external unit from receiving a given acknowledgment). Further, the hearing device 10 may provide longer usage time between recharging a power supply of the external unit 12, as the power that would otherwise be used to transmit, receive, and process the acknowledgement signal may instead be reserved for other functions of the external unit 12 and/or the stimulation unit 14.

As noted above, the stimulation unit 14 may determine whether it is associated with the external unit that generated the received stimulation data. In an example operation, the external unit 12 (as well as other similarly-configured external units, such as the external unit 13) periodically transmits an identification signal that identifies a target stimulation unit of transmitted stimulation data. In response to receiving the identification signal, the stimulation unit 14 may then determine whether it is the target stimulation unit of subsequently received stimulation data.

The identification signal could take any number of forms. By way of example, an audiologist or a manufacturer could assign to the stimulation unit 14 a unique unit identifier (e.g., an identification code) that distinguishes the stimulation unit 14 from all other stimulation units. The audiologist may also load the unit identifier into the external unit 12 as an implant identifier when fitting the hearing device 10 to the recipient, though the implant identifier could alternatively be loaded at the point of manufacture. The external unit 12 may thus include in an identification signal the implant identifier, and the stimulation unit 14 may process a received identification signal to determine whether the implant identifier matches the unit identifier. If the implant identifier matches the unit identifier, the stimulation unit 14 may then operate in the normal mode. But if the implant identifier does not match the unit identifier, the stimulation unit 14 operates in the safe mode.

Figure 2A:
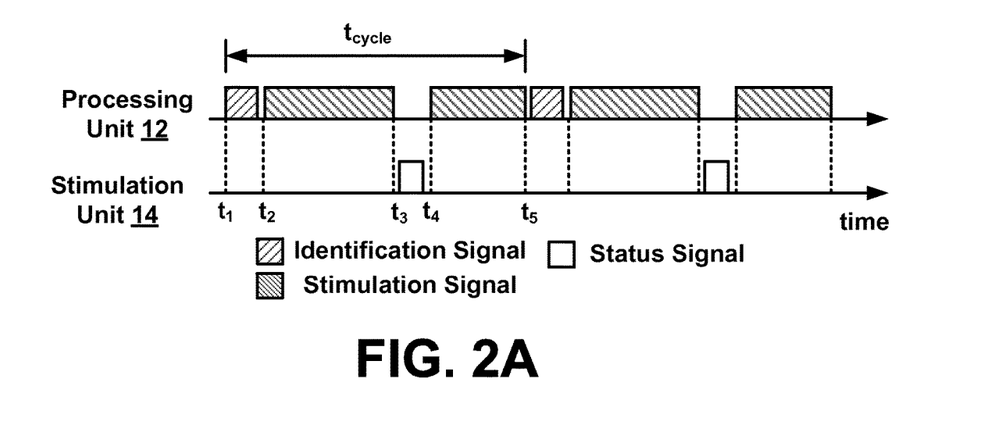
FIGS. 2A, 2B, and 2C are example timing diagrams for communications between components of example hearing systems.

In one example, the external unit 12 sends the identification signal and stimulation data in separate transmissions. To illustrate this example, FIG. 2A shows an example timing diagram of a communication scheme in which the external unit 12 and the stimulation unit 14 exchange data. As shown, the external unit 12 transmits an identification signal, which the stimulation unit 14 may receive and process to identify the implant identifier. After transmitting the identification signal, the external unit 12 begins transmitting stimulation signals at $t_2$. Upon determining that the implant identifier included in the identification signal matches the unit identifier, the stimulation unit 14 then processes subsequently received stimulation signals. Notably, in the illustrated example, the external unit 12 does not wait for an acknowledgment from the stimulation unit 14 between transmissions of stimulation signals. In other examples, however, the stimulation unit 14 may periodically acknowledge receiving one or more stimulation signals, and the external unit 12 may wait for such an acknowledgement signal before transmitting the next stimulation signal.

At time $t_3$, the external unit 12 switches to a receive mode in which it listens for a transmission from the stimulation unit 14. When operating in the normal mode, the stimulation unit 14 transmits a status signal to the external unit 12. The status signal may include information indicative of settings of parameters used by the stimulation unit 14 to process the received stimulation data, such as an identity of an active stimulation profile and/or an identity of each stimulation profile included in the plurality of available stimulation profiles.

The stimulation unit 14 may also include other information in the status signal. For example, if the stimulation unit 14 includes a rechargeable battery, then the stimulation unit 14 may include information indicative of a battery level (i.e., an amount of charge remaining in the battery). The external unit 12 then resumes transmitting, and the stimulation unit 14 resumes processing, stimulation data at $t_4$, thereby completing one cycle of the communication scheme at $t_5$. The external unit 12 and the stimulation unit 14 may continue performing additional cycles of the communication scheme. In general, a length of each cycle should be long enough to transmit multiple stimulation signals while accounting for the possibility that the stimulation unit 14 might not receive each, if not several, transmissions of the identification signal. For instance, a length of each cycle could take between 100 milliseconds or about 200 milliseconds.

Figure 2B:
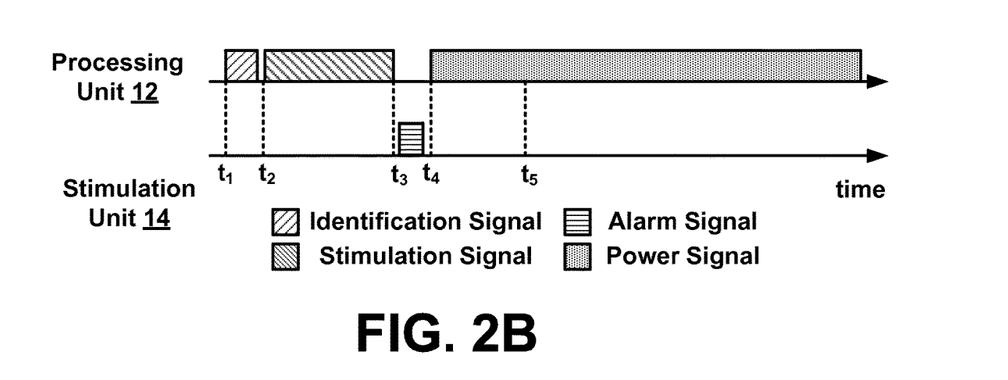

Turning now to FIG. 2B, an example communication scheme is shown depicting communications between an unassociated external unit 13 and the stimulation unit 14. The external unit 13 carries out the communication scheme in the same or a substantially similar manner as the external unit 12. Upon receiving and processing the identification signal, however, the stimulation unit 14 determines that the implant identifier does not match the unit identifier. In this case, the stimulation unit 14 switches to the safe mode and does not process the stimulation data included in subsequently received stimulation signals. Rather than generating a status signal, the stimulation unit 14 generates and transmits an alarm signal at time $t_3$. The stimulation unit 14 may include in the alarm signal information indicative of the implant identifier not matching the unit identifier, perhaps by including data corresponding to a fault code in the alarm signal.

Since the stimulation unit 14 does not process stimulation data while operating in the safe mode, the external unit 13 may stop generating and transmitting stimulation data upon receiving the alarm signal. The external unit 13 may, however, continue transmitting a power signal to the stimulation unit 14, thereby providing power to the stimulation unit 14 including a battery of a mostly or totally implantable hearing device.

Figure 2C:
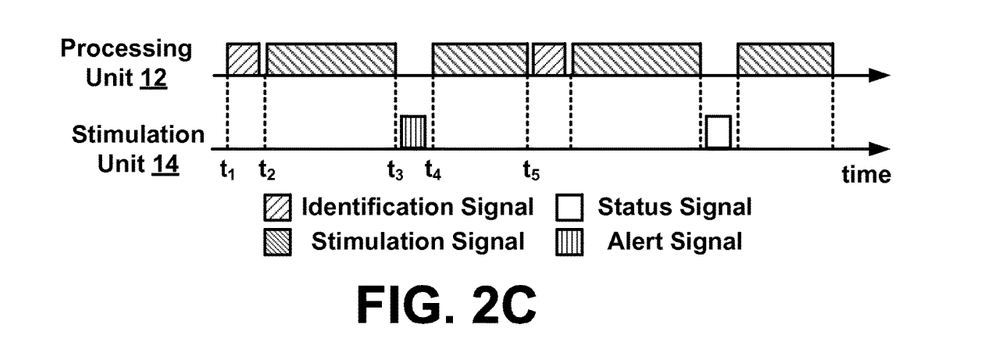

As another example, the stimulation unit 14 may determine that the implant identifier matches the unit identifier, but it may also determine that the active stimulation profile does not correspond to a stimulation profile stored in the stimulation unit 14. The stimulation unit 14 may make this decision upon processing either an identification signal or a stimulation signal, either of which could include information indicative of the active stimulation profile. In this case, the stimulation unit 14 may generate and transmit an alert signal to the external unit 12 in lieu of the status signal, as illustrated in FIG. 2C. The alert signal can include an indication of the active stimulation profile not corresponding to a stimulation profile included in the plurality of available stimulation profiles. Further, the stimulation unit 14 might include in the alert signal information indicative identity of each stimulation profile in the plurality of available stimulation profiles.

Unlike the case where the implant identifier does not match the unit identifier, however, the stimulation unit 14 may not stop processing received stimulation signals. Instead, the stimulation unit 14 may continue to process the received stimulation signals to determine whether the plurality of available stimulation profiles includes the active stimulation profile.

In the preceding examples, the identification signal and the stimulation signal are two separate signals. In other examples, however, the external unit 12 may not send a separate and distinct identification signal. Instead, the external unit 12 includes the implant identifier in the stimulation signals, perhaps in a header field, or even in the payload.

Further, the stimulation profiles described in the preceding examples may each be assigned a short, generic stimulation profile identifier. As another alternative then, each stimulation profile may be assigned a recipient-specific stimulation profile identifier. In this example, the stimulation unit 14 may not necessarily compare the implant identifier to the unit identifier when determining whether it can process received stimulation data. Instead, the stimulation unit 14 determines whether the stimulation profile identifier is included in the plurality of available stimulation profiles includes the active stimulation profile. As a result, the external unit 12 may not transmit the identification signal.

In practice, each identification signal, status signal, alarm signal, and alert signal is smaller (includes less data in total) than a stimulation signal, thereby minimizing the time needed to transmit such signals a time between transmissions of stimulation data to the stimulation unit 14. Preferably, the external unit 12 and the stimulation unit 14 transmit data signals in the form of data packets, with each data packet being transmitted as one or more frames. As such, a given stimulation signal generally comprises more data frames than a given identification signal, status signal, alarm signal, and/or alert signal. Note, however, that individual signals may comprise more or fewer frames than previous or subsequent signals.

Each packet includes a header and a payload. The header may including information indicate a type of signal (e.g., a stimulation signal, an identification signal, etc.), while the payload includes the data associated with the signal (e.g., stimulation data, the implant identifier, etc.). Additionally, the payload of some signals may include additional data. For example, the payload of an identification signal may include a current setting of a parameter used by the external unit to generate stimulation signals, such as a volume setting or the active stimulation profile. As another example, the external unit 12 may periodically include data indicative of the active stimulation profile in one or more stimulation signals. Note that in these examples, the data could alternatively be included in the header of an associated packet.

Figure 3:
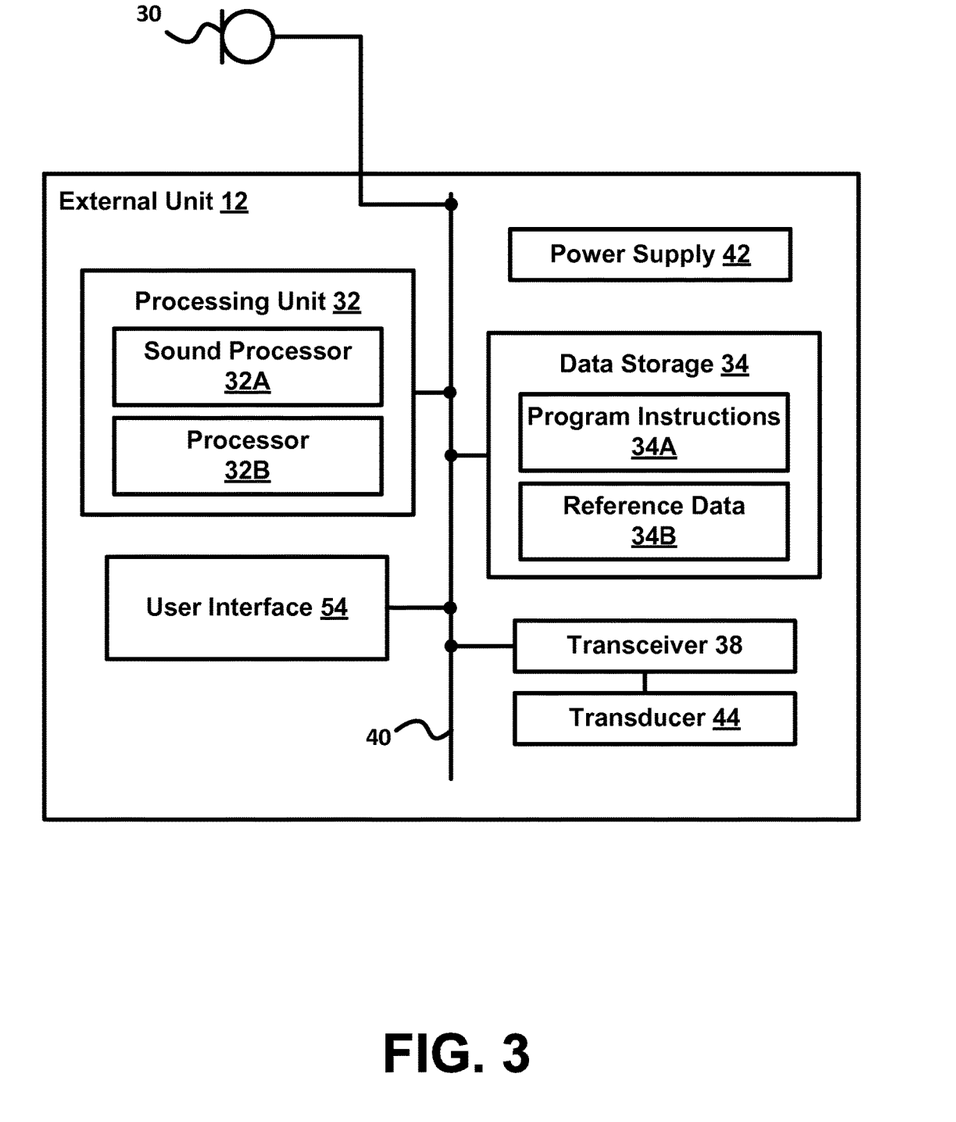
FIG. 3 is a simplified block diagram depicting components of an example external unit of a hearing device.

Turning now to FIG. 3, the external unit 12 includes a microphone (or other audio transducers) 30, a processing unit 32, data storage 34, an output component 36, a transceiver 38, which are communicatively linked together by a system bus, network, or other connection mechanism 40. The external unit 12 also includes a rechargeable battery 42 that provides power to the components of the external unit 12, and a transducer 44, such as an inductive coil, that is electrically connected to the transceiver 38 to facilitate communications with the stimulation unit 14 via the link 22, including transmission of a power signal to the stimulation unit 14.

In an example arrangement, the components are included in a single physical housing. In alternative arrangements, the components could be provided in multiple physical housings. For example, a behind-the-ear housing could include the microphone 30, the processing unit 32, the data storage 34, the output component 36, and the power supply 42, while a separate housing connected to the behind-the-ear housing, perhaps by a cable, could include the transducer 44. Other arrangements are possible as well.

In the arrangement as shown, the microphone 30 may be positioned to receive sounds, such as audio coming from an acoustic environment, and to provide a corresponding signal (e.g., electrical or optical, possibly sampled) to the processing unit 32. For instance, the microphone 30 may be positioned on an exposed surface of the housing of the external unit 12. Further, the microphone 30 may comprise additional microphones and/or other audio transducers, which could also be positioned on an exposed surface of the housing of the external unit 12.

The processing unit 32 may then comprise one or more digital signal processors (e.g., application-specific integrated circuits, programmable logic devices, etc.), as well as analog-to-digital converters. As shown, at least one such processor functions as a sound processor 32A, to process received sounds so as to enable generation of corresponding stimulation signals as discussed above. Further, another such processor 32B could be configured to receive and process inputs, such as a status signal, an alert signal, or an alarm signal received from the stimulation unit 14 via the transceiver 38. Alternatively, all processing functions could be carried out by the sound processor 32A itself.

The data storage 34 may then comprise one or more volatile and/or non-volatile storage components, such as magnetic, optical, or flash storage, and may be integrated in whole or in part with processing unit 32. As shown, the data storage 34 may hold program instructions 34A executable by the processing unit 32 to carry out various hearing device functions described herein, as well as reference data 34B that the processing unit 32 may reference as a basis to carry out various such functions.

By way of example, the program instructions 34A may be executable by the processing unit 32 to facilitate processing sounds received via the microphone 30 and to generate stimulation signals. For instance, the program instructions 34A may include instructions for processing the received sounds in order to select an active stimulation profile from the plurality of available stimulation profiles stored in the reference data 34B. The instructions may also include instructions for implementing a communication scheme, such as one of the communication schemes described with respect to FIGS. 2A-2C.

Additionally, the instructions may cause the processing unit 32 to provide a visual output via the output component 36. To this end, the output component 36 may include one or more light emitting diodes (LEDs), a liquid crystal display, an LED display, or the like. The processing unit 32, upon receiving an alarm signal or an alert signal from the stimulation unit 14, may cause the output component 36 to display an output indicative of the stimulation unit operating in the safe mode. For instance, if the output component includes an LED, the processing unit 32 may cause the LED to light or flash red. The instructions may further cause the processing unit 32 to automatically provide the visual output.

The reference data 34B may include settings of adjustable sound-processing parameters, such as a current volume setting, a current sound-processing strategy (e.g., a strategy for combining one or more audio signals and/or selecting frequency channels at which to generate stimuli), and an active stimulation profile. Moreover, the reference data 34B may include the plurality of available stimulation profiles. The processing unit 32 may access the reference data 34B when selecting the active stimulation profile and/or when processing signals received from the stimulation unit 14. Note that the listed examples of parameters are illustrative in nature and do not represent an exclusive list of possible sound-processing parameters and/or system parameters.

Figure 4:
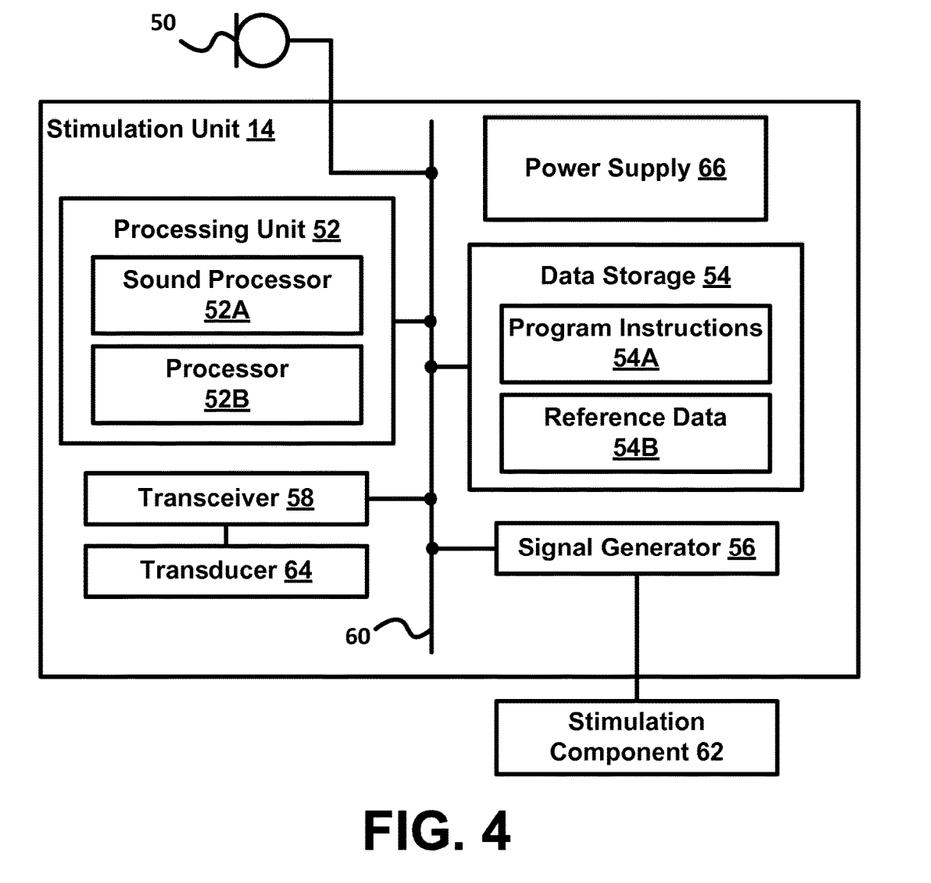
FIG. 4 is a simplified block diagram depicting components of an example stimulation unit of a hearing device.

Turning now to FIG. 4, the stimulation unit 14 includes a microphone (or another audio transducer) 50, a processing unit 52, data storage 54, a signal generator 56, and a transceiver 58, which are communicatively linked together by a system bus, network, or other connection mechanism 60. The stimulation unit 14 also includes a transducer 64, such as an inductive coil, that is electrically connected to the transceiver 58 to facilitate communications with the external unit 12 via the link 22. The stimulation unit 14 may further include a power supply 66, such as a rechargeable battery, that is configured to provide an alternate power source for the components of the stimulation unit 14 when power is not supplied by the external unit 12 (or another processing unit coupled to the stimulation unit 14).

In an example arrangement, each of these components, with the possible exception of the microphone 50 and the stimulator 62, are included in a single housing implanted in the recipient. Alternatively, the power supply 66 may be included in a separate housing implanted in the recipient to facilitate replacement. Other arrangements are possible as well.

In the arrangement as shown, the stimulation unit 14 is a totally implantable hearing device. Thus, the microphone 50 is positioned to receive audio input from an acoustic environment, and to provide a corresponding signal (e.g., electrical or optical, possibly sampled) to the processing unit 52. Further, the microphone 50 may include additional microphones and/or other audio transducers, which could also be positioned in the recipient's body to receive sounds from the ambient environment, or which could be positioned to receive internal sounds from the recipient's organs. As one example, the microphone 50 may be replaced with a transducer that detects a movement of one or more ossicles bones in the recipient's ear.

The processing unit 52 may be the same or substantially similar to the processing unit 32 described with respect to FIG. 4. As shown, the sound processor 52A may process received sounds from the microphone 50 to enable generation of corresponding stimuli when the stimulation unit 14 operates in the safe mode, as discussed above. In processing such sounds, the sound processor 52A may be configured to remove internal sounds (e.g., sounds from the recipient's organs) prior to generating the stimuli. Another such processor 62B could be configured to determine whether to operate the stimulation unit 14 in the normal mode or the safe mode by determining whether the processing unit 14 can process received stimulation data. To this end, the processor 52B may determine whether an implant identifier matches a unit identifier and whether the plurality of available stimulation profiles includes the active stimulation profile. The processor 52B may also process the received stimulation data to generate one or more stimuli when in operating in the normal mode, and the processor 52B may also generate the status signal. Additionally, the processor 52B may generate an alert signal or an alarm signal when operating in the safe mode. Alternatively, all processing functions, including functions for processing signals received from the external unit 12, could be carried out by the sound processor 32A itself.

The data storage 54 may, like the data storage 34, then comprise one or more volatile and/or non-volatile storage components, such as magnetic, optical, or flash storage, and may be integrated in whole or in part with processing unit 52. As shown, the data storage 54 may hold program instructions 54A executable by the processing unit 52 to carry out various hearing device functions described herein, as well as reference data 54B that the processing unit 52 may reference as a basis to carry out various such functions.

By way of example, the program instructions 54A may be executable by the processing unit 52 to facilitate determining whether to operate in the normal mode or the safe mode, and to generate stimuli associated with each mode as discussed above. For instance, the program instructions 54A may include instructions for determining whether an implant identifier matches a unit identifier, or to determine whether the plurality of available stimulation profiles includes the active stimulation profile. The program instructions 54A may also allow the processing unit 52 to process stimulation data using the active stimulation profile in order to generate electrical signals usable by the stimulation component 56 to generate one or more stimuli. Additionally, the program instructions 54A may include instructions for generating and transmitting a status signal, an alert signal, and/or an alarm signal.

The reference data 54B may include settings of adjustable sound-processing parameters, such as a current volume setting, a current sound-processing strategy, or the active stimulation profile, as well as the plurality of available stimulation profiles. Moreover, the reference data 54B may include stimulation data usable by the processing unit 52 to generate electrical signals suitable for generating one or more stimuli that cause the recipient to perceive an audible alarm. Note that the listed examples are illustrative in nature and do not represent an exclusive list of possible sound-processing parameters.

The stimulation component 56 may include a signal generator and other hardware suitable for generating stimuli. Upon receipt of electrical signals from the processing unit 52, the stimulation unit 56 may responsively cause the stimulator 62 to deliver one or more stimuli to a body part of the recipient, thereby causing the recipient to perceive at least a portion of a sound. By way of example, the stimulator 62 may be an electrode array inserted in the recipient's left cochlea, in which case the stimuli generated by the stimulation component 56 are electrical stimuli. As another example, the stimulator 62 could be a bone conduction device, and the stimulation component 56 may generate electromechanical stimuli. In yet another example, the stimulation component 62 may be a transducer inserted or implanted in the recipient's left middle ear, in which case the stimulation component 62 generates acoustic or electroacoustic stimuli. Other examples are possible as well.

Figure 5A:
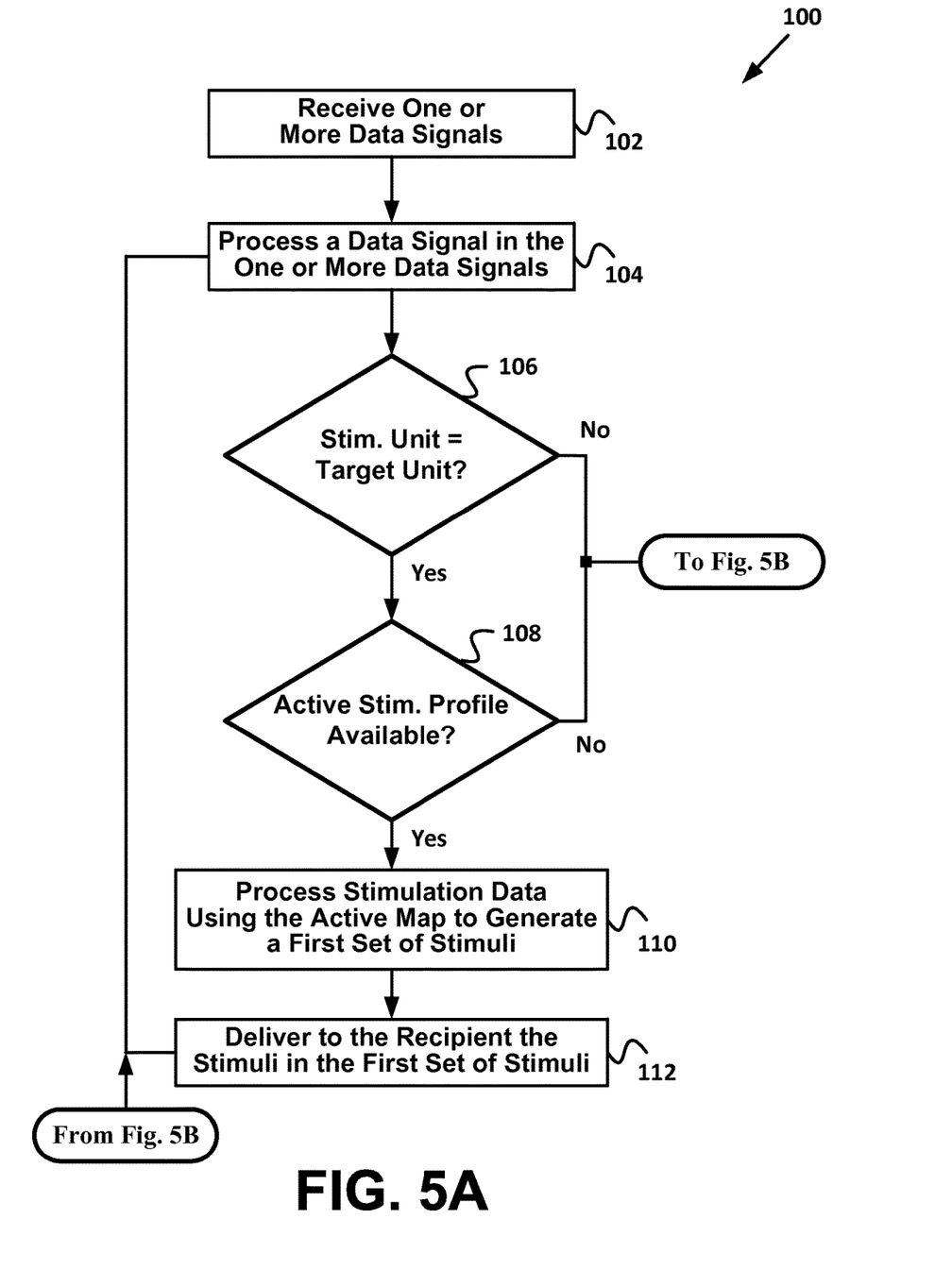
FIGS. 5A and 5B are flow charts depicting functions that can be carried out in accordance with the present disclosure.
Figure 5B:
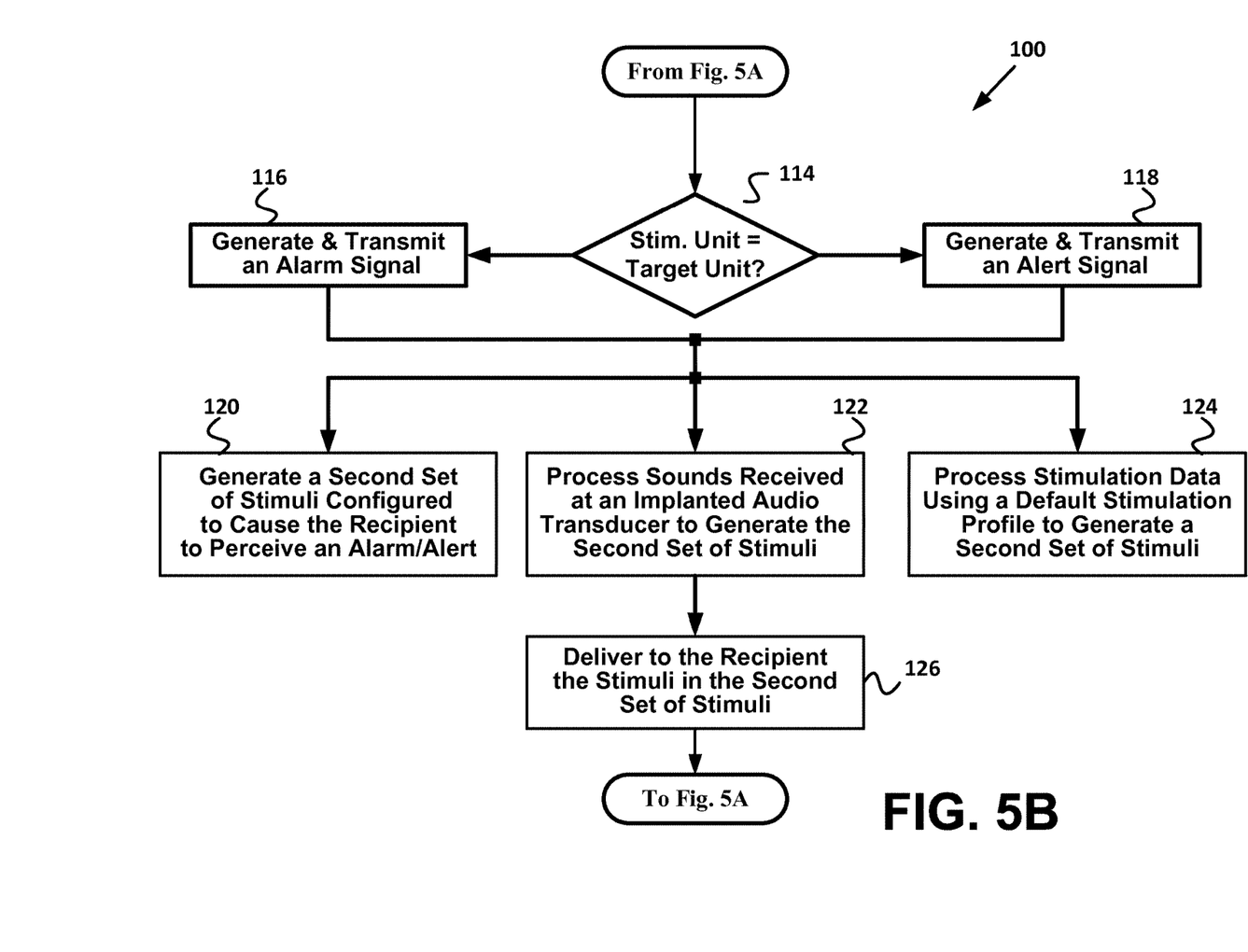

Finally, a flow chart is shown in FIGS. 5A and 5B to illustrate functions of a method 100 that can be carried out by a stimulation unit of a hearing device. For purposes of illustration only, these functions will be described with reference to the systems and components described with respect to FIGS. 1 and 2.

Starting with FIG. 5A, the method 100 begins at block 102 with the stimulation unit 14 receiving one or more data signals, with the one or more data signals including at least one stimulation signal. At block 104, the stimulation unit 14 processes a data signal included in the one or more data signals, which could be either an identification signal or a stimulation signal. In practice, the stimulation unit 14 processes the one or more data signals in the order they are received. The stimulation unit 14 then determines whether it is the target stimulation unit of the stimulation data and whether the active stimulation profile is accessible, at block 106 and 108, respectively.

When the processed data signal is an identification signal, the stimulation unit 14 determines that it is the target stimulation unit when the implant identifier matches the unit identifier. Similarly, when the processed data signal is a stimulation signal, the stimulation unit 14 determines whether the active stimulation profile is accessible by determining whether the plurality of available stimulation profiles includes the active stimulation profile indicated in the stimulation data.

If the stimulation unit 14 determines that it is the target stimulation unit and that the plurality of available stimulation profiles includes the active stimulation profile, the method 100 continues at block 110. If the processed data signal includes stimulation data, then the method 100 continues at block 110 with the external unit 14 processing the stimulation data using the active stimulation profile to generate a first set of one or more stimuli, and the stimulation unit 14 then delivering to the recipient the each stimulus in the first set of one or more stimuli, at block 112. After performing the steps of block 112, or upon the stimulation unit 14 determining that the processed data signal does not include stimulation data, the method 100 includes returning to block 104, where the stimulation unit 14 processes the data signal received after the processed data signal, thereby beginning another iteration of the method 100. In some examples, the stimulation unit 14 may begin another iteration of the method 100 while performing the steps of block 112, or even while performing the steps of block 110. Additionally, the stimulation unit 14 may periodically perform the steps of block 102 to receive additional data signals.

If the stimulation unit 14 determines that either it is not the target stimulation unit for the received stimulation data or the active map is not accessible, the method 100 continues with the stimulation unit 14 operating in the safe mode, which is shown in FIG. 5B. At block 114, the stimulation unit 14 determines whether it is the target stimulation unit, as described with respect to block 106. If the stimulation is the target stimulation unit, the stimulation unit 14 proceeds to block 116, where the stimulation unit 14 generates and transmits to the external unit 12 an alert signal. Otherwise, the stimulation unit 14 proceeds to block 118 and generates and transmits to the external unit 12 an alarm signal The stimulation unit 14 then performs at least one or more of blocks 120, 122, or 124. At block 120 for instance, the stimulation unit 14 generates a second set of stimuli configured to cause the recipient to perceive an audible alert or alarm. In an example in which the stimulation unit 14 is a totally implantable hearing device, the stimulation unit 14 could process a sound received at an implanted microphone to generate the second set of stimuli, at block 122. And at block 124, the stimulation unit 14 may process the received stimulation data using a default stimulation profile to generate the second set of stimuli. Note that the stimulation unit 14 may not process the received stimulation data to generate the second set of stimuli when perform the steps of blocks 120 or 122.

Finally, the stimulation unit 14 may deliver to the recipient the stimuli in the second set of stimuli, at block 126. The stimulation unit 14 may then return to block 104 to process the next data signal in the received one or more data signals.

While various aspects and embodiments have been disclosed herein, other aspects and embodiments will be apparent to those skilled in the art. The various aspects and embodiments disclosed herein are for purposes of illustration and are not intended to be limiting, with the scope being indicated by the following claims.

What is claimed is:
1. A method comprising:
 receiving at a stimulation unit of a hearing device one or more data signals, the one or more data signals comprising at least one stimulation signal that includes stimulation data;

the stimulation unit processing a data signal in the one or more data signals to determine whether the stimulation unit is a target stimulation unit of the stimulation data; and the stimulation unit operating in one of (i) a normal mode if the stimulation unit is the target stimulation unit of the stimulation data or (ii) a safe mode other than the normal mode if the stimulation unit is not the target stimulation unit of the stimulation data, wherein operating in the normal mode comprises the stimulation unit (i) using an active stimulation profile to process the stimulation data and (ii) based on the processed simulation data, generating one or more stimuli, and (iii) delivering the one or more stimuli to a recipient, and wherein operating in the safe mode comprises the stimulation unit not processing the stimulation data using the active stimulation profile.

2. The method of claim 1, wherein the stimulation unit operating in the safe mode further comprises:

generating an alarm signal, wherein the alarm signal includes information indicative of the stimulation unit operating in the safe mode; and transmitting to a processing unit the alarm signal.

3. The method of claim 1, wherein:

the one or more data signals further comprise an identification signal that includes information indicative of a implant identifier, wherein the processed data signal is the identification signal, and to determine whether the stimulation unit is the target stimulation unit of the stimulation data, the method further comprises the stimulation unit: (i) determining whether the implant identifier matches a unit identifier assigned to the stimulation unit, (ii) determining that the stimulation unit is the target stimulation unit of the stimulation data when the implant identifier matches the unit identifier, and (iii) determining that the stimulation unit is not the target stimulation unit of the stimulation data when the implant identifier does not match the unit identifier.

4. The method of claim 3, wherein the one or more data signals further comprise a plurality of stimulation signals, each stimulation signal including stimulation data usable by the stimulation unit to generate one or more stimuli, and wherein the stimulation unit receives the identification signal prior to at least one stimulation signal included in the plurality of stimulation signals.

5. The method of claim 1, wherein the processed data signal includes information indicative of the active stimulation profile, and wherein, to determine whether the stimulation unit can process the stimulation data, the method further comprising the stimulation unit (i) determining whether the active stimulation profile is included in a plurality of available stimulation profiles usable by the stimulation unit to process the stimulation data, wherein each available stimulation profile includes a set of parameters usable by the stimulation unit to process the stimulation data, (ii) operating in the normal mode when the active stimulation profile is included in the plurality of available stimulation profiles, and (iii) operating in the safe mode when the active stimulation profile is not included in the plurality of available stimulation profiles.

6. The method of claim 5, wherein the processed data signal further includes the stimulation data.

7. The method of claim 1, wherein, in response to determining that the operating mode is the safe mode, the method further comprises:

the stimulation unit processing a sound received at an implanted audio transducer, wherein the implanted audio transducer is a component of the stimulation unit;

based on the processed sound, the stimulation unit generating the one or more stimuli; and delivering the one or more stimuli to the recipient.

8. The method of claim 1, wherein:

the stimulation unit operating in the safe mode further comprises the stimulation unit generating one or more stimuli configured to cause the recipient to perceive an audible alarm;

and the stimulation unit delivering the one or more stimuli to the recipient;

the stimulation unit is the target stimulation unit of the stimulation data, and the method further comprising:

operating the stimulation unit in the normal mode to evoke a hearing percept based on a map that is pre-stored in the hearing device before the reception of the one or more data signals.

9. The method of claim 1, wherein:

the stimulation unit is the target stimulation unit of the stimulation data, and the method further comprising:

capturing ambient sound using a sound capture device;

converting the ambient sound to an electromagnetic signal;

operating the stimulation unit in the normal mode to evoke a hearing percept based on the electromagnetic signal and based on the map that is pre-stored in the hearing device before the reception of the one or more data signals.

10. The method of claim 1, wherein:

the stimulation unit includes a transceiver, wherein the action of processing the data signal and the action of processing the stimulation data are executed by components of the stimulation unit separate from the transceiver.

11. A non-transitory computer-readable medium having stored therein instructions executable by a computing device to cause the computing device to perform functions comprising:

determining whether a first identifier matches a second identifier, wherein the first identifier is included in a data signal transmitted by a processing unit of a hearing device and the second identifier is accessible to a stimulation unit of the hearing device;

if at least the first identifier matches the second identifier, (i) generating a first set of stimuli by processing a first set of stimulation data using an active stimulation profile selected by the processing unit, and (ii) causing a stimulation component of the stimulation unit to deliver the one or more stimuli to the recipient; and if at least the first identifier does not match the second identifier, (i) generating a second set of stimuli by one of (1) processing a second set of stimulation data, or (2) processing the first set of stimulation data using a default stimulation profile, and (ii) causing the stimulation component of the stimulation unit to deliver the stimuli in the second set of stimuli, wherein the first set of stimulation data is generated by the processing unit and the second set of stimulation data is generated by a component other than the processing unit, and wherein the active stimulation profile and the default stimulation profile are different stimulation profiles.

12. The non-transitory computer-readable medium of claim 11, wherein the first identifier is an implant identifier that identifies a target stimulation unit, and wherein the second identifier is a unit identifier that is unique to the stimulation unit.

13. The non-transitory computer-readable medium of claim 11, wherein the first identifier is included in an identification signal, and wherein the first set of stimulation data is included in one or more stimulation signals received at the stimulation unit after the identification signal is received.

14. The non-transitory computer-readable medium of claim 11, wherein the second set of stimulation data comprises stimulation data for generating an audible alert.

15. The non-transitory computer-readable medium of claim 11, wherein, if the first identifier does not match the second identifier, the functions further comprise generating an alarm signal that includes information indicative of the first identifier not matching the second identifier, and causing a component of the stimulation unit to transmit the alarm signal to the processing unit.

16. The non-transitory computer-readable medium of claim 11, wherein:
the first identifier identifies the active stimulation profile selected by the processing unit,
the second identifier identifies a stimulation profile included in a plurality of available stimulation profiles accessible to the stimulation unit to generate the one or more stimuli, and
the first identifier matches the second identifier if the plurality of available stimulation profiles includes the active stimulation profile, and
the first identifier does not match the second identifier if the plurality of available stimulation profiles does not include the active stimulation profile.

17. The non-transitory computer-readable medium of claim 16, wherein, if the first identifier does not match the second identifier, the functions further comprise generating an alert signal that includes information indicative of the first identifier not matching the second identifier, and causing a component of the stimulation unit to transmit to the processing unit the alarm signal.

18. The non-transitory computer-readable medium of claim 17, wherein the alert signal further comprises information identifying each stimulation profile included in the plurality of available stimulation profiles.

19. The non-transitory computer-readable medium of claim 11, wherein the non-transitory computer-readable medium further has stored therein instructions executable by the computing device to cause the computing device to control the stimulation unit to withhold stimulation by not generating stimulation based on received stimulation data if at least the first identifier does not match the second identifier when the stimulation unit is in a safe mode.

20. A stimulation unit of a hearing device comprising:
a data storage configured to store at least two available stimulation profiles, wherein each available stimulation profile includes a set of fixed parameters for generating a plurality of stimuli;
a stimulation component configured to stimulate a body part in an auditory pathway of the recipient; and
a processor configured to:
(i) receive and process a stimulation signal, wherein the stimulation signal includes stimulation data and an active stimulation profile;
(ii) access the data storage to determine that the active stimulation profile is one of the at least two internal stimulation profiles;
(iii) determine, based on the stimulation data and using the active stimulation profile, a stimulus deliverable by the stimulation component to the recipient; and
(iv) cause the stimulation component to deliver the determined stimulus to the recipient.

21. The stimulation unit of claim 20, wherein the data storage stores a unit identifier that is unique to the stimulation unit, and wherein after receiving the stimulation signal, the processor is further configured to:
receive an identification signal that includes an implant identifier;
determine that the implant identifier does not match the unit identifier; and
in response to determining that the implant identifier does not match the unit identifier, operate in a safe mode in which the stimulation unit does not process stimulation data received.

22. The stimulation unit of claim 21, further comprising at least one audio transducer implanted in a body of the recipient, and wherein, to operate in the safe mode, the processor is further configured to:
process a sound received at the at least one audio transducer;
process the sound to determine an additional stimulus deliverable by the stimulation component; and
cause the stimulation component to deliver the additional stimulus to the recipient.

23. The stimulation unit of claim 21, wherein, to operate in the safe mode, the processor is further configured to cause the stimulation component to deliver one or more additional stimuli to the body part, wherein the one or more additional stimuli are configured to cause the recipient to perceive an audible alarm.

24. The stimulation unit of claim 20, wherein the processor is further configured to:
access the data storage to determine that the active stimulation profile is not one of the at least two internal stimulation profiles;
upon a determination that the active stimulation profile is not one of the at least two internal stimulation profiles, use a default stimulation profile to determine a stimulus deliverable by the stimulation component instead of the active stimulation profile.

* * * * *